United States Patent
Yamamoto et al.

(10) Patent No.: US 8,986,184 B2
(45) Date of Patent: Mar. 24, 2015

(54) APPARATUSES AND METHODS FOR FOLDING AN ABSORBENT ARTICLE

(75) Inventors: Yoichiro Yamamoto, Cologne (DE); Thomas Ludwig Woschnik, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 1023 days.

(21) Appl. No.: 13/051,210

(22) Filed: Mar. 18, 2011

(65) Prior Publication Data

US 2011/0251040 A1 Oct. 13, 2011

Related U.S. Application Data

(60) Provisional application No. 61/322,333, filed on Apr. 9, 2010.

(51) Int. Cl.
| | | |
|---|---|---|
| *B31F 1/10* | (2006.01) | |
| *B31B 1/26* | (2006.01) | |
| *B65H 45/16* | (2006.01) | |
| *A61F 13/15* | (2006.01) | |
| *B31B 1/58* | (2006.01) | |

(52) U.S. Cl.
CPC ....... *A61F 13/15747* (2013.01); *B65H 2801/57* (2013.01); *B65H 45/165* (2013.01); *B65H 45/167* (2013.01)
USPC ............................. 493/418; 493/424; 493/454

(58) Field of Classification Search
CPC .................... A61F 13/15757; A61F 13/15764; B65H 45/06; B65H 45/16; B65H 45/09
USPC ................................... 493/405, 441, 450, 454
See application file for complete search history.

(56) References Cited

U.S. PATENT DOCUMENTS

| | | | |
|---|---|---|---|
| 3,927,875 A | 12/1975 | Winnemoller et al. | |
| 4,425,173 A | 1/1984 | Frick | |
| 4,694,978 A | 9/1987 | Westphal et al. | |
| 4,739,910 A | 4/1988 | Westphal et al. | |
| 4,940,464 A | 7/1990 | Van Gompel et al. | |
| 5,013,378 A | 5/1991 | Farah | |
| 5,092,861 A | 3/1992 | Nomura et al. | |
| 5,108,017 A * | 4/1992 | Adamski et al. ................. | 223/37 |
| 5,167,897 A | 12/1992 | Weber et al. | |
| 5,246,433 A | 9/1993 | Hasse et al. | |
| 5,360,420 A | 11/1994 | Cook et al. | |
| 5,569,234 A | 10/1996 | Buell et al. | |
| 5,599,335 A | 2/1997 | Goldman et al. | |
| 5,643,588 A | 7/1997 | Roe et al. | |
| 5,674,216 A | 10/1997 | Buell et al. | |
| 5,702,551 A | 12/1997 | Huber et al. | |
| 5,779,831 A | 7/1998 | Schmitz | |
| 5,785,804 A | 7/1998 | Kovacs et al. | |
| 5,795,433 A | 8/1998 | Niedermeyer | |

(Continued)

FOREIGN PATENT DOCUMENTS

| | | | |
|---|---|---|---|
| WO | WO 2007/029195 A2 | 3/2007 | |
| WO | WO 2009/032995 A1 | 3/2009 | |

OTHER PUBLICATIONS

PCT International Search Report and Written Opinion, dated Jun. 20, 2011, 13 pages.

*Primary Examiner* — Gloria R Weeks
(74) *Attorney, Agent, or Firm* — Charles R. Matson

(57) ABSTRACT

Aspects of the present disclosure involve methods and apparatuses for folding absorbent articles.

12 Claims, 10 Drawing Sheets

(56) References Cited

U.S. PATENT DOCUMENTS

| | | |
|---|---|---|
| 5,842,964 A | 12/1998 | Huber et al. |
| 5,897,545 A | 4/1999 | Kline et al. |
| 5,904,277 A | 5/1999 | Niedermeyer |
| 5,904,802 A | 5/1999 | Niedermeyer |
| 5,957,908 A | 9/1999 | Kline et al. |
| 5,968,025 A | 10/1999 | Roe et al. |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,183,576 B1 | 2/2001 | Couillard et al. |
| 6,283,905 B1 | 9/2001 | Singh |
| 6,385,946 B1 | 5/2002 | Singh |
| 6,410,129 B2 | 6/2002 | Zhang et al. |
| 6,426,444 B2 | 7/2002 | Roe et al. |
| 6,497,032 B2 | 12/2002 | Maxton et al. |
| 6,511,569 B1 | 1/2003 | Nixon et al. |
| 6,513,221 B2 | 2/2003 | Vogt et al. |
| 6,565,500 B1 | 5/2003 | Hailey et al. |
| 6,565,691 B2 | 5/2003 | Tomsovic et al. |
| 6,586,652 B1 | 7/2003 | Roe et al. |
| 6,596,107 B2 | 7/2003 | Stopher |
| 6,617,016 B2 | 9/2003 | Zhang et al. |
| 6,627,787 B1 | 9/2003 | Roe et al. |
| 6,717,656 B2 | 4/2004 | Chien et al. |
| 6,730,188 B2 | 5/2004 | Sanders |
| 6,808,478 B1 | 10/2004 | Singh |
| 6,825,393 B2 | 11/2004 | Roe et al. |
| 6,854,624 B2 | 2/2005 | Vogt et al. |
| 6,861,571 B1 | 3/2005 | Roe et al. |
| 6,893,388 B2 * | 5/2005 | Reising et al. ............... 493/231 |
| 7,175,584 B2 | 2/2007 | Maxton et al. |
| 7,384,386 B2 | 6/2008 | Sosalla |
| 7,390,373 B2 | 6/2008 | Karlsson et al. |
| 7,399,266 B2 * | 7/2008 | Aiolfi et al. ................. 493/424 |
| 7,955,244 B2 | 6/2011 | Burns, Jr. et al. |
| 8,020,598 B2 | 9/2011 | Kirita et al. |
| 8,469,869 B2 * | 6/2013 | Yamamoto ................... 493/442 |
| 2003/0233082 A1 | 12/2003 | Kline et al. |
| 2005/0209079 A1 | 9/2005 | Belmann |
| 2006/0276320 A1 | 12/2006 | Aiolfi et al. |
| 2009/0094941 A1 | 4/2009 | Burns, Jr. et al. |
| 2009/0098995 A1 | 4/2009 | Burns, Jr. et al. |
| 2010/0050411 A1 | 3/2010 | Yamamoto |
| 2011/0039678 A1 | 2/2011 | Burns, Jr. et al. |
| 2011/0245060 A1 | 10/2011 | Burns, Jr. et al. |
| 2011/0251040 A1 | 10/2011 | Yamamoto et al. |
| 2012/0015790 A1 | 1/2012 | Yamamoto et al. |
| 2012/0015791 A1 | 1/2012 | Yamamoto |
| 2012/0015792 A1 * | 1/2012 | Yamamoto ................... 493/454 |

* cited by examiner

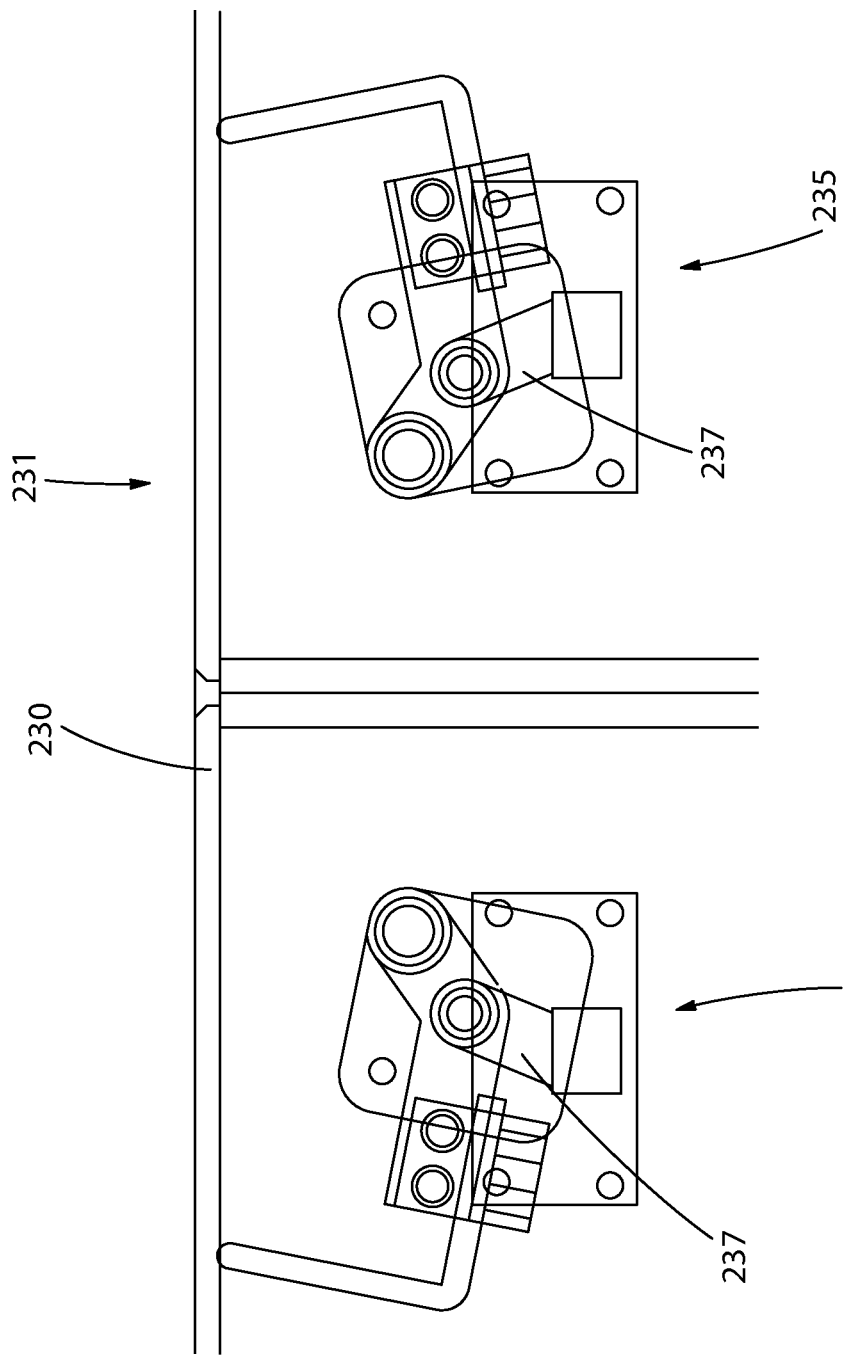

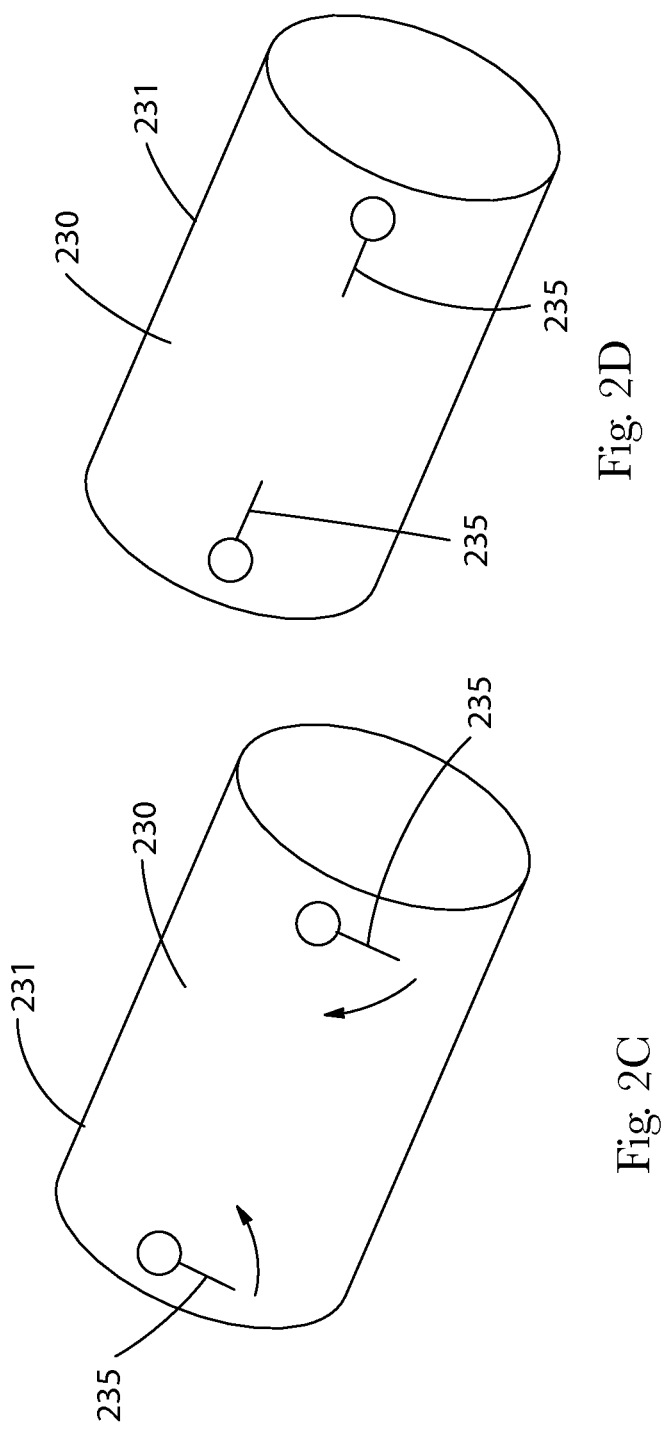

APPARATUSES AND METHODS FOR FOLDING AN ABSORBENT ARTICLE

CROSS REFERENCE TO RELATED APPLICATION

This application claims the benefit of U.S. Provisional Application No. 61/322,333, filed on Apr. 9, 2010, which is hereby incorporated by reference.

FIELD OF THE INVENTION

The present disclosure relates to methods and apparatuses for manufacturing articles, and more particularly, methods and apparatuses for folding absorbent articles.

BACKGROUND OF THE INVENTION

Disposable absorbent articles, such as diapers, pull-on diapers, training pants, adult incontinence pads, wipes, facial tissue, toilet tissue, napkins, paper towels and the like are often manufactured and/or packaged on a high-speed production line where individual articles may move along a production path at a speed of hundreds of meters per minute. During the manufacturing and/or packaging process the disposable absorbent articles may undergo a folding process. For example, a disposable diaper may undergo a bifolding process prior to being placed in a package. In a bifolding process, an article is folded into two parts. The article may be folded in half in the longitudinal direction such that two opposing portions of the article are brought together in a face-to-face configuration. Some manufacturers of disposable diapers may provide a bifolded diaper that has a front end edge that is substantially aligned with a back end edge of the diaper. However, current manufacturing practices often do not provide the desired degree of alignment between the diaper end edges, resulting in a diaper that may have undesirable characteristics in the marketplace. The problem may be further compounded for so-called "training pant" diapers which, after being folded into a U in the same or similar way as conventional diapers, are joined permanently, e.g., sealed, along the lateral portions to form a closed annular girdle enabling the diaper to be used pant-fashion. The high degree of precision for folding training pants may require increased accuracy beyond that of a traditional taped diaper, so that the lateral portions of the training pant, which are to be joined permanently, are configured with the desired overlap.

In some processes for providing a folded absorbent article, a portion of a production line for making absorbent articles may include a primary roll for carrying the absorbent article. The primary roll may apply a suction force, e.g. vacuum, to hold the absorbent article in the proper position during the folding process. Such processes may also utilize one or more secondary rolls for pulling a portion of the absorbent article, typically the leading end portion, off of the primary roll. The secondary roll(s) may employ vacuum pressure to pull the leading portion of the absorbent article off of the primary roll and hold the pulled off portion to the secondary roll surface of the second roll. As the manufacturing process or converting operation continues, more of the leading end portion of the article may continue to be pulled off of the primary roll and attached to the secondary roll. Next, the article may be subjected to forces that pull the leading and trailing end portions of the article in substantially opposite directions. For example, clips or other mechanical holding means may be used to hold the middle portion of the absorbent article to the surface of the primary roll in order to provide sufficient force to pull the leading end portion of the article from of the secondary roll. Typically, once the leading end portion of the article is pulled from or released by the secondary roll, the leading end portion will travel back toward the primary roll to continue through the folding process. However, when the leading end portion of the article is pulled/released from the secondary roll, it may be subjected to turbulence or other forces that cause the leading end portion to move about in an uncontrolled manner, potentially resulting in a folded article with undesirably misaligned end and/or side edges.

In order to overcome the problems associated with the uncontrolled movement of the leading end portion when the leading end portion is separated from the secondary roll, processes may utilize a transfer roll or conveyor configured with a vacuum system to receive the leading end portion of the absorbent article and transfer it back to the primary roll. In some instances, the surface of the transfer roll or conveyor includes a porous belt or other foraminous surface that allows the suction force of the vacuum system to be exerted at the surface of the conveyor or roll. The surface speed of the transfer conveyor or roll may be constant, and in some instances is set to match the surface speed of the primary roll. In this way, the leading end portion of the article can be transferred back to the primary roll at about the same speed as the trailing end portion is travelling, potentially reducing the chance for misalignment of the leading and trailing end portions during folding. However, when the leading end portion of the article is separated from the secondary roll, the relative speeds of the leading end portion and the surface of the transfer conveyor or roll may still be substantially different. While the transfer roll or conveyor may be able to capture the leading end portion and hold it to the conveyor or roll surface with vacuum pressure and thereby minimize uncontrolled movement, the leading end portion may still end up in an undesirable configuration (e.g., wrinkled, bunched, crooked, etc.) due to the rapid acceleration typically experienced by the leading edge when it contacts the continuously moving transfer roll or conveyor.

In further efforts to overcome the problems resulting from the rapid acceleration of the leading end portion of the absorbent article when contacting the transfer roll or conveyor, some processes may utilize a transfer roll or conveyor that decelerates the transfer roll or conveyor to substantially match the speed of the leading end portion of the absorbent article when transferring the leading portion from the secondary roll to the transfer roll or conveyor. Once the leading end portion is transferred to the transfer roll or conveyor, the transfer roll or conveyor is accelerated to substantially match the speed of the primary roll. However, before the leading end portion of the article is pulled/released from the secondary roll rotating at a constant speed, the outer surface of the rotating secondary roll will move relative to or slip under leading end portion of the article. Frictional forces resulting from the relative movement or slippage between the leading end portion of the article can cause in undesirable resulting configurations. For example, leading end portions of articles with laterally extending components, such as diaper ears or fasteners, may become wrinkled or crooked.

SUMMARY OF THE INVENTION

Aspects of the present disclosure involve methods and apparatuses for folding absorbent articles.

In one form, an apparatus may be adapted for folding articles advancing in a machine direction along a cross directional fold line, wherein each article has a leading end portion and a trailing end portion and having a first surface disposed opposite of a second surface. The apparatus may include: a drum having an outer surface, the drum adapted to rotate the outer surface at a first surface speed, wherein the outer surface of the drum is adapted to receive the first surface of each article and transport each article in the machine direction; a first conveyor assembly comprising: a first vacuum conveyor comprising a movable surface adapted to travel at the first surface speed, wherein the movable surface of the first conveyor is adapted to receive the second surface of the leading end portion of each article from the drum; a second vacuum conveyor comprising a movable surface adapted to travel at the first surface speed and at a second surface speed, wherein the movable surface of the first vacuum conveyor is adapted to receive the second surface of the leading end portion of each article from the first conveyor; and a second conveyor assembly comprising: a third vacuum conveyor comprising a movable surface adapted to travel at the first surface speed and at the second surface speed, wherein the movable surface of the third vacuum conveyor is adapted to receive the first surface of the leading end portion of each article from the second conveyor; a fourth vacuum conveyor comprising a movable surface adapted to travel at the first speed, wherein the movable surface of the fourth vacuum conveyor is adapted to receive the first surface of the leading end portion of each article from the third conveyor.

In another form, a method for folding articles advancing in a machine direction along a cross directional fold line, each article having a leading end portion and a trailing end portion and having a first surface disposed opposite of a second surface, may include the steps of: receiving an article onto a drum having an outer surface such that the first surface of the article is engaged with the outer surface of the drum; rotating the drum to move the outer surface at a first surface speed and transport the article in the machine direction; engaging the second surface of the leading end portion of the article with a first conveyor comprising a movable surface traveling at the first speed; transferring the leading end portion of the article from the drum to the first conveyor; transferring the second surface of the leading end portion of the article from the first conveyor to a second conveyor comprising a movable surface traveling at the first speed; decelerating the movable surface of the second conveyor to a second speed; moving a third conveyor comprising a movable surface traveling at the second speed to engage the first surface of the leading end portion of the article; transferring the leading end portion of the article from the second conveyor to the third conveyor; accelerating the movable surface of the third conveyor from the second speed to the first speed; transferring first surface of the leading end portion of the article from the third conveyor to a fourth conveyor comprising a movable surface traveling at the first speed; and transferring the leading end portion of the article from the fourth conveyor onto the trailing end portion of the article on the drum.

BRIEF DESCRIPTION OF THE DRAWINGS

FIG. 2A is a first cut-away view of bifold movable clamps used with the apparatus shown in FIG. 2.

FIG. 2C is an isometric view of a folding drum and a second embodiment of bifold clamps in an open position.

FIG. 2D is an isometric view of the folding drum and the second embodiment of bifold clamps of FIG. 2C in a closed position.

DETAILED DESCRIPTION OF THE INVENTION

Figure 1:
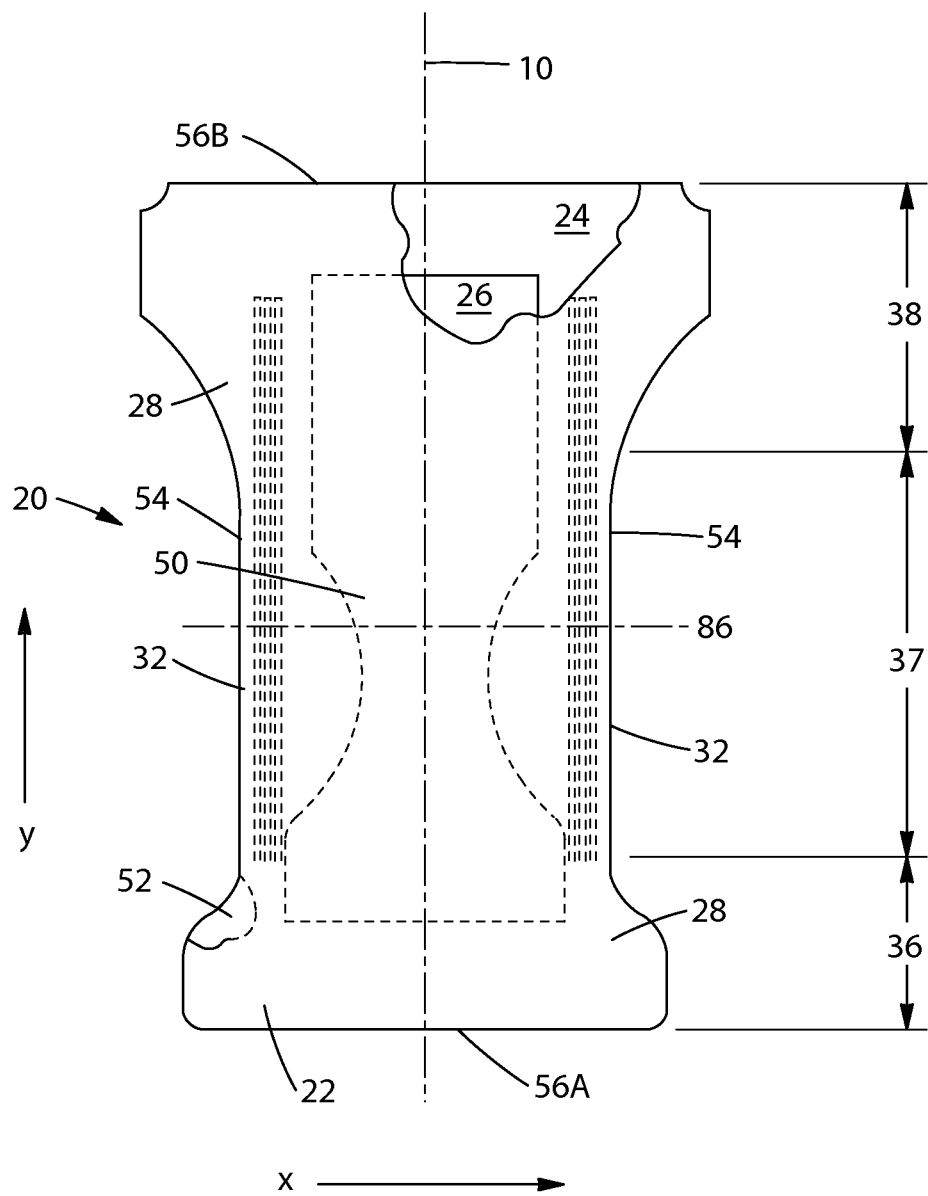
FIG. 1 is a partial cut away view of a diaper in its flat-out, uncontracted state with the body-facing surface oriented toward the viewer.

The following term explanations may be useful in understanding the present disclosure:

"Absorbent article" is used herein to refer to consumer products whose primary function is to absorb and retain soils and wastes. Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Diaper" is used herein to refer to an absorbent article generally worn by infants and incontinent persons about the lower torso.

"Bifold" means the leading edge portion and the trailing edge portion of an article on a production line are brought together in a face-to-face configuration along a fold line as the article moves in the machine direction of travel.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element (s) is formed (joined and positioned) in a particular place or position as a macro-unitary structure with other elements or as a separate element joined to another element.

"Fold line" means the portion of an article about which the article is bifolded to form a leading end portion and a trailing end portion. The fold line typically extends from one longitudinal edge to the other longitudinal edge in the lateral direction. In certain embodiments, the fold line may correspond to the lateral centerline of the article.

"Holding an article to the surface of a roll" means employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., the bifold conveyor assembly described hereinbelow.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Leading end portion" means that portion of a bifolded article that is forward of the fold line in the machine direction.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal." "Lateral" refers to a direction running from a longitudinal edge to an opposing longitudinal edge of an article and generally at a right angle to the longitudinal direction. Directions within 45 degrees of the lateral direction are considered to be "lateral."

"Machine direction" (also "MD" or "length direction") means the direction that is parallel to the direction of travel of an article or article element as it is processed in the forming apparatus. In a bifold process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll and/or conveyor, may travel in two different directions simultaneously. In this example, both directions of travel may be considered the machine direction. The "cross machine direction" or "cross direction" (also "CD" or "width direction") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface in which the object lies or on which the object rests. A force applied in a direction within 45° of the perpendicular direction may be considered a peel force.

"Shear force" means the force applied to an object in a direction that is substantially parallel to the plane of the surface in which the object lies or on which the object rests. A force applied in a direction within 45° of the parallel direction may be considered a shear force.

"Trailing end portion" refers to that portion of a bifolded article that is after the fold line in the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper typically is folded about the lateral centerline with the interior of one waist region in surface to surface contact with the interior of the opposing waist region without fastening or joining the waist regions together. Suitable taped diapers are disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" (also referred to as "training pant", "pre-closed diaper", "diaper-pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Suitable pants are disclosed in various suitable pant configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

"Vacuum" and "vacuum pressure" mean a pressure of less than 13000 Newtons per square meter.

Aspects of the present disclosure involve methods and apparatuses for manufacturing articles, and more particularly, methods and apparatuses for folding absorbent articles. Embodiments of the apparatuses and methods disclosed herein may be configured to provide for a relatively smooth transfer, deceleration, and acceleration of different portions of an absorbent article from one device to another during the folding process. In some embodiments, different components of the folding apparatus having movable surfaces may be configured to hold and move different portions of an absorbent article at different speeds with little or no relative movement between movable surfaces and respective portions of the absorbent article.

As discussed below in more detail, embodiments of a folding apparatus may include a folding drum, a first conveyor assembly, and a second conveyor assembly that operate to fold articles advancing in a machine direction along a cross directional fold line. As discussed in more detail below, the folding drum may include an outer surface adapted to receive each article thereon. The folding drum rotates to move the outer surface at a first speed and transports the articles in a machine direction. As the folding drum rotates, a leading end portion of each article is transferred to a movable surface traveling at the first speed on the first conveyor assembly. At the same time, a trailing end portion of the article remains on the outer surface of the rotating folding drum. The movable surface of the first conveyor assembly and the leading end portion of the article then decelerate to a second speed. In some instances, movable surface may decelerate to a second speed of zero or stopped. As the movable surface of the first conveyor assembly decelerates, the second conveyor assembly moves toward the leading end portion of the article. As the leading end portion of the article reaches the second speed, the second conveyor assembly engages the leading end portion of the article, which in turn, transfers the leading end portion of the article to a movable surface of the second conveyor assembly. The movable surface of the second conveyor assembly and leading end portion of the article are then accelerated back to the first speed. And the leading end portion of the article is transferred from the second conveyor assembly onto the trailing end portion of the article on the rotating folding drum.

Although much of the present disclosure is provided in the context of manufacturing absorbent articles, it is to be appreciated that the apparatuses and methods disclosed herein may be applied to the manufacture of various types of articles and products. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, pre-moistened cloths, paper towels, dryer sheets and dry-cleaning clothes such. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, training and pull-on pants, adult incontinence briefs and undergarments, feminine hygiene garments such as panty liners, absorbent inserts, and the like, toilet paper, tissue paper, facial wipes or clothes, and toilet training wipes. Still other examples of products may include packaging components and substrates and/or containers for laundry detergent and coffee, which may be produced in pellets or pouches and may be manufactured in a converting or web process or even discreet products produced at high speed such as high-speed bottling lines, cosmetics, razor blade cartridges, and disposable consumer batteries.

Although it is to be appreciated that the folding apparatuses and methods according to the present disclosure may be used to fold taped diapers and diaper pants, the following description of an absorbent article in the form of a diaper and associated components helps provide additional context to the subsequent discussion of folding methods and apparatuses. FIG. 1 shows a partial cut-away view of a diaper 20 shown in a flat-out, uncontracted state (e.g., with no elastic induced contraction). The diaper 20 may include a liquid pervious topsheet 22; a liquid impervious backsheet 24 joined with the topsheet 22; an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54, a first end edge 56A corresponding to the first waist region 36, and an opposing second end edge 56B corresponding to the second waist region 38. The diaper 20 may include a longitudinal centerline 10 (e.g., positioned midway between the longitudinal side edges 54) and a lateral centerline 86 (e.g., positioned midway between opposing end edges 56A and 56B) orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate bifolding of the diaper 20, but need not necessarily be so. According to the methods and apparatuses herein, the diaper 20 may be bifolded along the lateral centerline 86 such that the first waist region 36 and the second waist region 38 are positioned in a face-to-face relationship along the inner surface 50. A bifolded diaper according to certain embodiments may have the first end edge 56A and the second end edge 56B aligned. A bifolded diaper according to certain embodiments may have the longitudinal side edges 54 partially or entirely aligned (e.g., the longitudinal side edges 54 may be aligned only in those areas that are visible to a consumer and/or are to be permanently joined together).

Figure 2:
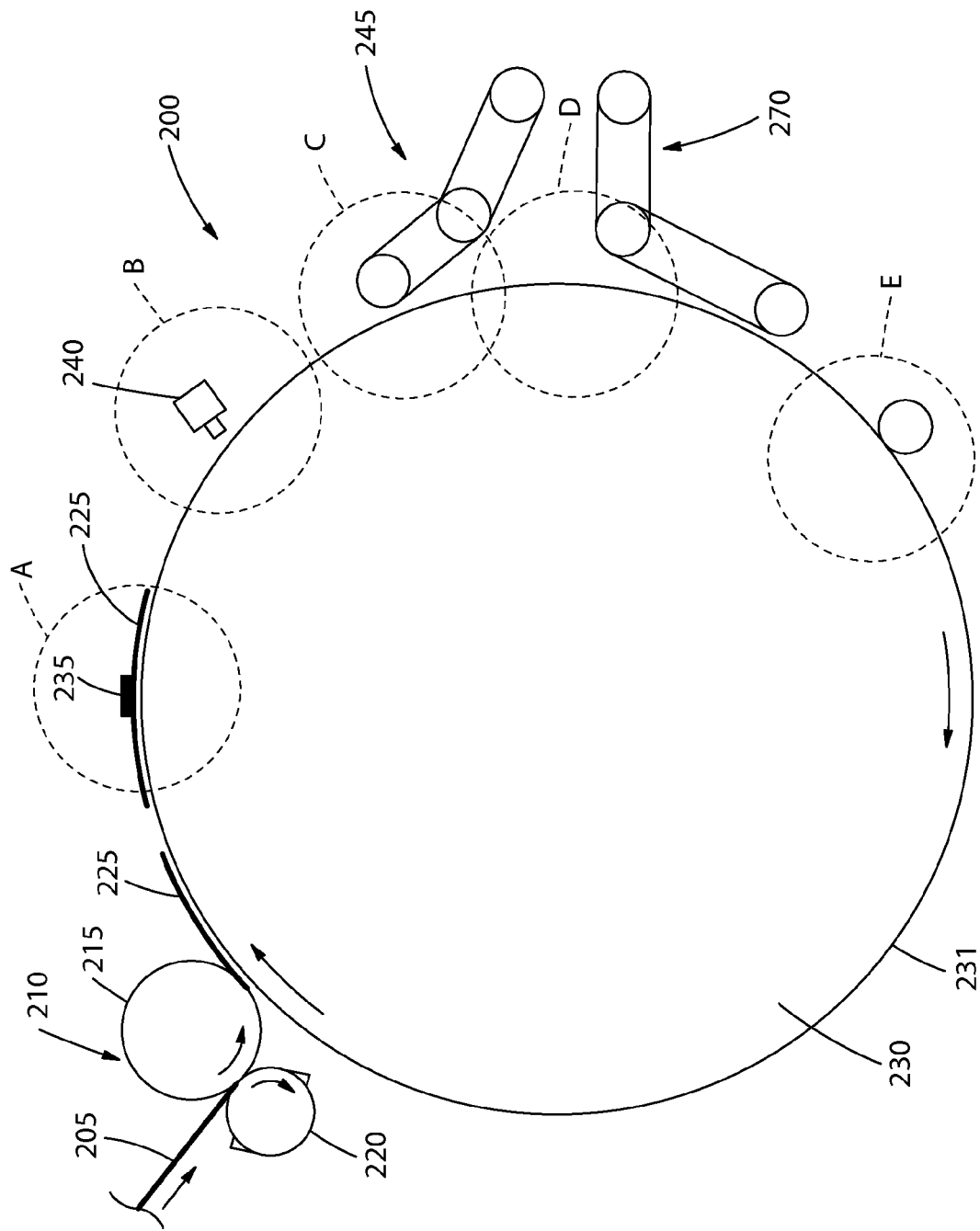
FIG. 2 is a schematic side view of an embodiment of a folding apparatus.

FIG. 2 shows an embodiment of a folding apparatus 200 including a folding drum 230, a first conveyor assembly 245, and a second conveyor assembly 270. The folding apparatus in FIG. 2 is shown and described herein as folding absorbent articles 225. An example of the absorbent article 225 being processed by the folding apparatus 200 may be in the form of the diaper described and depicted in FIG. 1. As previously discussed, it is to be appreciated that other types and configurations of articles may be processed by the folding apparatus 200. In addition, the folding apparatus 200 is generally described herein with respect to a single article 225, but it is to be understood that the folding apparatus is capable of operating at speeds that allow for the processing of more than one article. Where the article to be bifolded is an absorbent article 225, the absorbent article 225 may be conveyed and placed onto the rotating folding drum 230. In some embodiments, a continuous web of absorbent articles 205 may be conveyed to a cutting unit 210 that cuts the continuous web into discrete absorbent articles 225. The discrete absorbent articles may then be transferred to the folding drum 230. The cutting unit 210 shown in FIG. 2 includes a knife roll 220 and an anvil roll. In other embodiments, a continuous web of absorbent articles 205 may be conveyed and transferred to the folding drum 230 first, and then cut into separate absorbent articles 225 while on the folding drum. As such, the folding drum may also be configured as an anvil roll. The absorbent articles 225 may have various different longitudinal lengths. For example, some absorbent articles 225 may have a longitudinal length of 480 mm.

Figure 3:
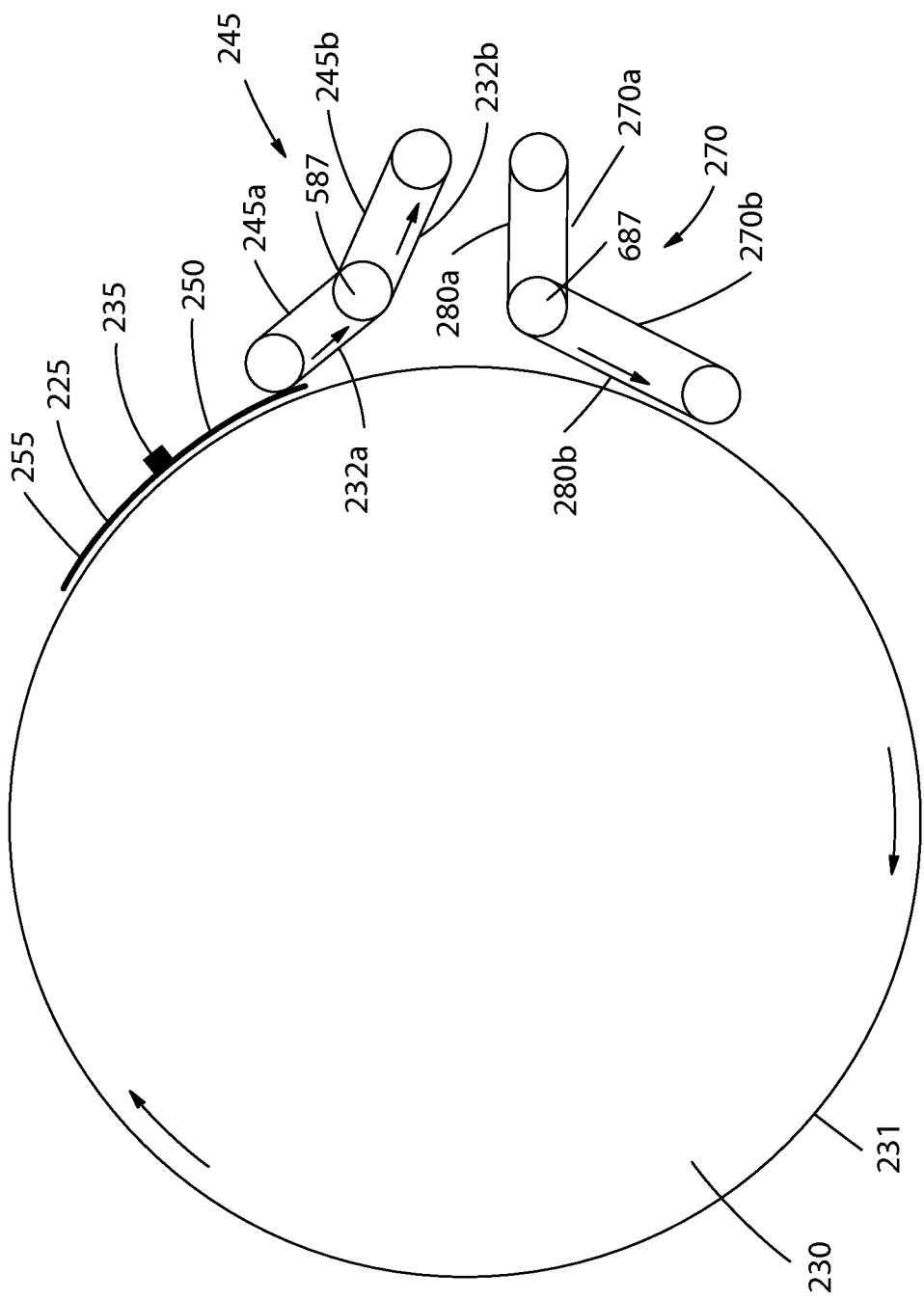
FIG. 3 is a detailed schematic view the article folding apparatus of FIG. 2 showing a leading end portion of an article on a folding drum and engaging a first conveyor assembly.

The folding drum 230 may be configured as a vacuum drum that rotates at a constant or variable speed. Although the folding drum 230 is shown in FIG. 3 as rotating in a clockwise direction, it is to be appreciated that the folding drum 230 can be configured to rotate in a counterclockwise direction. Various configurations of vacuum drums can be used with the apparatuses and methods herein, such as described for example, in U.S. Pat. Nos. 5,904,802 and 6,513,221. The rotation speed of the folding drum 230 may be set to various different speeds. In some instances, the rotational speed of the folding drum 230 is set as function of the line speed of the manufacturing process. It is also to be appreciated that the folding drum may be configured in different sizes. For example, some embodiments utilize what may be referred to as a 5-up drum, i.e., a drum capable of fitting five articles at once. In some embodiments of a 5-up drum, each cycle includes folding one article, and for each cycle the folding drum may rotate between 70° and 74°, and in some instances, the drum rotates 72° for each cycle. In some embodiments, the drum may be a 3-up drum, i.e., capable of fitting three article at once, and may rotate between 118° and 122° for each cycle, and in some instances, 120°. In some embodiments, other size folding drums may be configured depending on the dimensions of the article being folded.

As shown in FIG. 2, the folding drum 230 includes an outer circumferential surface 231 that is adapted to hold and transport absorbent articles 225 thereon in the machine direction. In some embodiments, the absorbent article 225 may be transferred to the outer surface 231 of the folding drum 230 such that the topsheet of the article 225 is facing outward and the backsheet of the article 225 is held against the outer surface 231 of the folding drum 230. The absorbent article 225 may be oriented in relation to a predetermined path such that a leading end portion 250 of the absorbent article 225 is downstream of a trailing end portion 255 of the absorbent article 225 (i.e., the leading end portion 250 enters a particular manufacturing process or sequence of processes before the trailing end portion 255). It should be appreciated that the folding drum and/or absorbent articles may be configured with various different relative cross directional widths. For example, in some configurations, the width of the folding drum 230 may be greater than width of the article and associated article components. In other configurations, the width of the folding drum 230 may be narrower than width of the article and/or one or more article components. In some embodiments, a portion of the absorbent article 225 may even hang over one or more edges of the folding drum 230. In one nonlimiting example, a portion of the side panel of a diaper may hang over from 12 mm to 15 mm.

As discussed in more detail below, the folding apparatus may control the positioning and movement of the absorbent article 225 throughout the folding process such that particular portions of the absorbent article 225 do not interfere with or disrupt the bifold processing performed on the absorbent article 225. For example, the folding drum 230 may exert a holding force on the absorbent article. In some embodiments, the folding drum exerts a vacuum force to hold portions of the absorbent article 225 in a substantially flat, uncontracted state along the outer surface 231 of the folding drum 230 until the absorbent article 225 is folded and/or assembled.

As the absorbent article 225 moves along with the rotation of the folding drum 230, the article 225 may be exposed to a variety of processes. The dashed circles A-E shown in FIG. 2 correspond with the general locations where the various processes may be performed as the folding drum 230 rotates.

Figure 2B:
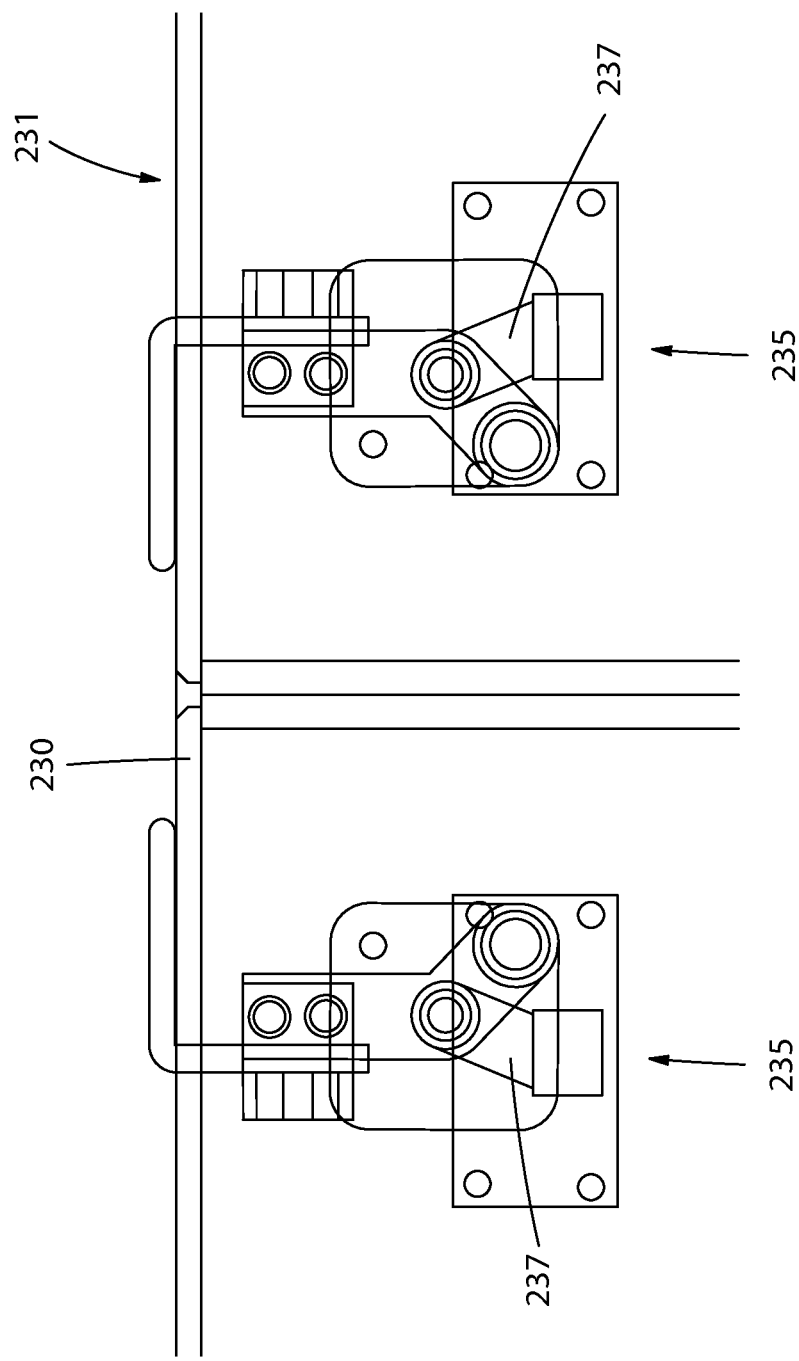
FIG. 2B a first cut-away view of bifold movable clamps used with the apparatus shown in FIG. 2.

At location A, the article 225 may be secured to the folding drum 230 with a securing force. For example, a mechanical force may be provided by movable bifold clamps 235 or other mechanical securing system. FIGS. 2A and 2B show an example embodiment of a set of movable bifold clamps 235 that may be used. The bifold clamps 235 may be controlled and driven by one or more cams 237 from an open position, as shown in FIG. 2A, to a closed position, as shown in FIG. 2B. As shown in FIGS. 2A and 2B, the bifold clamps 235 may pivot inward from the sides of the folding drum 230 and secure the article 225 to the outer surface 231 of the folding drum 230. The bifold clamps may engage the article 225 at a particular position, for example, at or near a lateral centerline of the article 225 along at least a portion of the longitudinal side edges. By way of example only, the diaper 20 shown in FIG. 1 may be secured to the outer surface 231 of the folding drum 230 by the bifold clamps 235 near the lateral centerline 86 of the diaper 20 along at least of portion of the longitudinal side edges 54. The bifold clamps 235 may continue to secure the article 225 to the surface of the folding drum 230 at or near a particular portion of the absorbent article 225 until after the article 225 is folded. An example of a clamping system may be found in U.S. Pat. No. 7,399,266. It is to be appreciated that embodiments having a securing force provided by one or more vacuum forces, electrostatic forces, and/or magnetic forces working alone or in combination with each other or the bifold clamps 235 may also be used with the disclosed folding apparatus 200.

FIGS. 2C and 2D show another embodiment of the bifold clamps 235 that may be used with the folding drum 230. FIG. 2C shows the bifold clamps in an open position, and FIG. 2D shows the bifold clamps rotated to a closed position. As shown in FIGS. 2C and 2D, the bifold clamps 235 may rotate inwardly toward each other along the outer surface 231 of the folding drum 230.

With reference to FIG. 2, the folding drum 230 may rotate from location A and transport the article 225 to a process station, such as an adhesive applicator 240 at location B where an adhesive may optionally be applied. From location B, the folding drum 230 may continue to rotate and transport the article 225 toward the first conveyor assembly 245 at location C, also referred to herein as a peel conveyor assembly. The peel conveyor assembly may be configured with one or more vacuum conveyors having one or more movable surfaces 232. As discussed in more detail below, the peel conveyor assembly may be configured to peel or remove a leading end portion 250 of the article while traveling at a first speed from the outer surface 231 of the folding drum, decelerate with the leading end portion 250 to a second speed, and transfer the leading end portion 250 to the second conveyor assembly 270.

As shown in FIG. 3, the peel conveyor assembly 245 may include a first conveyor 245a and a second conveyor 245b. The first conveyor 245a includes a movable surface 232a, and the second conveyor 245b includes a movable surface 232b. In some embodiments, the first and second conveyors 245a, 245b may each include a movable foraminous conveyor belt configured in an endless loop. In addition, it is to be appreciated that the first and second vacuum conveyors 245a, 245b may each include one or more discrete movable surfaces 232a, 232b, respectively, configured as, for example, one or more belts configured in an endless loop and driven by a drive mechanism. The first and second vacuum conveyors 245a, 245b may be configured to provide suitable vacuum pressure to receive, hold, and/or transfer the leading end portion 250 of the article 225. The belt speed of the first conveyor 245a may substantially match the surface speed 231 of the folding drum. After receiving the leading end portion 250 from the folding drum 230, leading end portion 250 of the article 225 is carried toward and transferred to the second vacuum conveyor 245b. At the time of transfer, the belt speed of the second conveyor 245b may substantially match the belt speed of the first conveyor 245a. In turn, the belt speed of the second conveyor 245b may be decreased to substantially match the slowing speed of the leading end portion 250 of the article 225.

The first and second conveyors 245a, 245b may also be configured to share one or more common elements such as, for example, a shaft 587. Shaft 587 may be coupled to, e.g., a variable speed drive motor and configured to drive the endless belt 232b of the second vacuum conveyor 245b at one or more speeds. The shaft 587 may also include one or more free-spinning rollers or pulley-like elements that enable the shaft 587 to simultaneously operate as an idler roll for the endless belt 232a of the first vacuum conveyor 245a. The first vacuum conveyor 245a may be driven by, e.g., a constant speed motor that drives the first vacuum conveyor belt 232a at, e.g., the surface speed of the folding drum 230, through a mechanical coupling. By sharing shaft 587, the first and second vacuum conveyor belts 232a, 232b may be configured to overlap at one end in the machine direction, and thereby facilitate transfer of the leading end portion 250 from the first vacuum conveyor 245a to the second vacuum conveyor 245b. During transfer of the leading end portion 250 from the first vacuum conveyor 245a to the second vacuum conveyor 245b, the vacuum pressures on the first and second conveyors 245a, 245b may be configured (e.g., decreased/increased and/or stopped/started) to facilitate transfer of the leading end portion 250. After receiving the leading end portion 250, the second vacuum conveyor 245b transports the leading end portion 250 away from the folding drum 230 at a variable speed. While the first and second conveyors 245a, 245b may share a common element, it is to be understood that the first and second conveyors 245a, 245b may also be configured as discrete components. It is also to be appreciated that other embodiments of the peel conveyor assembly 245 may be configured as a single continuous variable speed conveyor, as opposed to having separate first and second conveyors. In addition, the first conveyor 245a may also be configured as a variable speed conveyor.

As discussed below, rotation of the folding drum 230 causes the outer surface 231 to travel at a first speed. In turn, the first conveyor 245a is configured such that the movable surface 232a travels at or approximately the first speed, and the second conveyor 245b is configured such that the movable surface 232b can travel at the first speed as well as lower second speed. The folding drum 230 and the peel conveyor assembly 245 may be positioned such that folding drum outer surface 231 is adjacent the movable surface 232a. The minimum distance between the folding drum outer surface 231 and the movable surface 232a may be sized such that an article 225 can pass between the surfaces 231, 232a with little or no resistance. For example, at location C, a leading end portion 250 of the article 225 may come into contact with the movable surface 232a without substantially impeding the progress of the article 225. As mentioned above, the movable surface 232a of the first conveyor 245a may travel at a constant first speed such that the movable surface 232a and the folding drum 230 have similar or the same surface speed, e.g., within 0.5%, 0.2%, 0.1%, or even identical.

FIG. 3 shows a detailed view of the folding drum 230 and the peel conveyor assembly 245 as the article 225 travels toward the first conveyor 245a. As shown in FIG. 3, the leading end portion 250 is the first portion of the article 225 to arrive at first conveyor 245a. The first conveyor 245a may be configured to apply a peel-force (e.g., vacuum pressure/suction) to attract and hold part of the leading end portion 250 when the leading end portion 250 is, e.g., at or in the vicinity a peel point 265 between the movable surface 232a and outer surface 231 of the folding drum 230. In some embodiments, the peel-force exerted by the first conveyor 245a may pull a portion of the leading end portion 250 of the article 225 away from the folding drum 230. As the leading end portion 250 of the article 225 is pulled away from the folding drum 230, any force exerted by the folding drum 230 on the leading end portion 250 of the article 225 may be simultaneously or sequentially removed or reduced.

Figure 4:
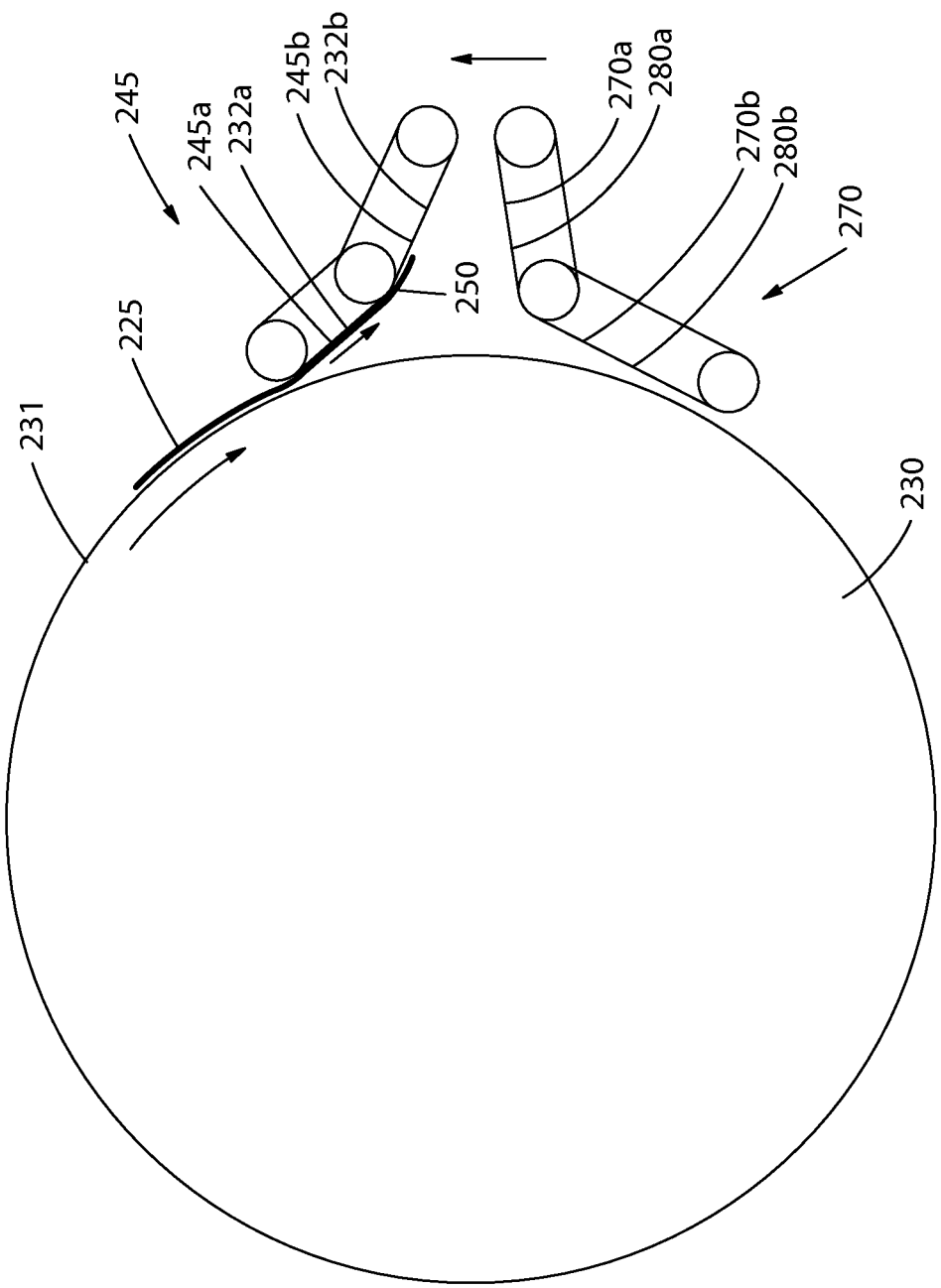
FIG. 4 is a detailed schematic view the article folding apparatus of FIG. 3 showing the leading end portion of the article transferred to the first conveyor assembly.

Referring to FIGS. 2-4, the folding drum may continue to rotate from location C to location D, wherein the leading end portion 250 article 225 is removed from the outer surface 231 of the folding drum 230 up to the portion of the article 225 secured by the bifold clamps 235 and at least some portion(s) adjacent thereto. At the same time, the leading end portion 250 article 225 travels from the first conveyor 245a to the movable surface 232b of the second conveyor 245b. The portion of the article 225 secured by the bifold clamps 235 may correspond approximately to the lateral centerline of the article 225, such as shown for example in FIG. 5. As a portion of the article 225 is transferred to the peel conveyor assembly 245, the holding force exerted by the folding drum 230 on the article 225 or portions of the article 225 may be reduced or removed accordingly. In embodiments utilizing movable bifold clamps 235, the bifold clamps 235 may remain in the closed position, thereby permitting the article 225 to only be transitioned to the first conveyor 245a up to the portion of the article secured by bifold clamps 235 ("clamped portion" 236). The remaining portion of the article 225, i.e., the trailing end portion 255 may be held against the folding drum outer surface 231 by the holding force and/or securing force, for example, vacuum force and/or bifold clamps 235.

With continued reference to FIGS. 2-4, as the folding drum 230 continues to rotate, the bifold clamps 235 and the clamped portion 236 of the article 225 continue to move with the folding drum outer surface 231. When the bifold clamps 235 reach a particular position relative to the peel conveyor assembly 245, the bifold clamps may exert a force such as, for example, a shear force on the leading end portion 250. The shear force exerted on the leading end portion 250 may be in a direction that is substantially different from or even opposite the direction of travel of the movable surface 232b of the second conveyor 245b. Thus, the leading end portion 250 may begin to slow down and/or even stop moving. To help prevent the leading end portion 250 of the article from slipping on the movable surface 232b of the second conveyor 245b as the leading portion 250 decelerates, the speed of the movable surface 232b is correspondingly slowed and/or stopped along with the leading end portion 250.

As such, in some embodiments, the leading end portion of the article 250 traveling at a first speed is transferred from the outer surface 231 of the folding drum 230 to the movable surface 232a of the first conveyor 245a traveling at or about the first speed. The leading end portion 250 of the article 225 travels along the movable surface 232a at the first speed and is transferred to the movable surface 232b of the second conveyor 245b traveling at or about the first speed. As the folding drum 230 continues to rotate and exerts a shear force on the leading end portion 250 of the article 225, causing the leading end portion 250 to decelerate from the first speed to a second speed, the movable surface 232b of the second conveyor 245b is correspondingly decelerated to the second speed. It is to be appreciated that the second may be equal to zero wherein the leading end portion 250 is stopped. As discussed in more detail with reference to FIGS. 6 and 7, once the leading end portion 250 of the article 225 is slowed to the second speed, the leading end portion 250 may be transferred from the second conveyor 245b to the second conveyor assembly 270, also referred to herein as a bifold conveyor assembly. From the bifold conveyor assembly 270, the leading end portion 250 of the article 225 is transferred back to the folding drum 230 and placed in a face-to-face relationship with the trailing end portion 255 of the article 225.

As shown in FIG. 2, the bifold conveyor assembly 270 may include a first conveyor 270a and a second conveyor 270b. The first conveyor 270a includes a movable surface 280a, and the second conveyor 270b includes a movable surface 280b. In some embodiments, the first and second conveyors 270a, 270b may each include a movable foraminous conveyor belt configured in an endless loop. In addition, it is to be appreciated that the first and second vacuum conveyors 270a, 270b may each include one or more discrete movable surfaces 280a, 280b, respectively, configured as, for example, one or more belts configured in an endless loop and driven by a drive mechanism. The first and second vacuum conveyors 270a, 270b may be configured to provide suitable vacuum pressure to receive, hold, and/or transfer the leading end portion 250 of the article 225. As discussed in more detail below, the belt speed of the first conveyor 270a may be variable so as to substantially match a decelerated speed of the leading end portion 250 on the second conveyor 245b of the peel conveyor assembly 245. After receiving the leading end portion 250 from the peel conveyor assembly 245, the leading end portion 250 of the article 225 is accelerated, carried toward, and transferred to the second vacuum conveyor 270b. At the time of transfer, the belt speed of the first conveyor 270a may substantially match the belt speed of the second conveyor 270b.

The first and second conveyors 270a, 270b may also be configured to share one or more common elements such as, for example, a shaft 687. Shaft 687 may be coupled to, e.g., a variable speed drive motor and configured to drive the endless belt 280a of the first vacuum conveyor 270a at one or more speeds. The shaft 687 may also include one or more free-spinning rollers or pulley-like elements that enable the shaft 687 to simultaneously operate as an idler roll for the endless belt 280b of the second vacuum conveyor 270b. The second vacuum conveyor 270b may be driven by, e.g., a constant speed motor that drives the second vacuum conveyor belt 280b at, e.g., the surface speed of the folding drum 230, through a mechanical coupling. By sharing shaft 687, the first and second vacuum conveyor belts 280a, 280b may be configured to overlap at one end in the machine direction, and thereby facilitate transfer of the leading end portion 250 from the first vacuum conveyor 270a to the second vacuum conveyor 270b. During transfer of the leading end portion 250 from the first vacuum conveyor 270a to the second vacuum conveyor 270b, the vacuum pressures on the first and second conveyors 280a, 280b may be configured (e.g., decreased/increased and/or stopped/started) to facilitate transfer of the leading end portion 250. After receiving the leading end portion 250, the second vacuum conveyor 270b transports the leading end portion 250 toward the folding drum 230 at a constant speed. While the first and second conveyors 270a, 270b may share a common element, it is to be understood that the first and second conveyors 270a, 270b may also be configured as discrete components. It is also to be appreciated that other embodiments of the bifold conveyor assembly 270 may be configured as a single continuous variable speed conveyor, as opposed to having separate first and second conveyors. In addition, the second conveyor 270b may also be configured as a variable speed conveyor.

As discussed in more detail below with reference to location D in FIG. 2 as well as FIGS. 5, 6, and 7, the leading end portion 250 of the article 225 is transferred from the peel conveyor assembly 245 to the first conveyor 270a of the bifold conveyor assembly 270. As such, the first conveyor 270a may include a variable speed vacuum conveyor surface 280a adapted to selectively engage the leading end portion 250 while disposed on the peel conveyor assembly 245. In the present context, "engaging" is generally meant as coming into close proximity (e.g., <10 cm, up to and including physically contacting the absorbent article 225) such that suction present at the surface of the first vacuum conveyor 270a can be applied to the absorbent article 225. As previously discussed, the movable surface 280a may be slowed or even temporarily stopped from moving prior to, while, and/or after engaging the leading end portion 250. In some embodiments, the movable surface of the conveyor 280a and the leading end portion 250 may be moving in substantially the same direction (i.e., toward the folding drum 230). As the leading end portion 250 is separated from the peel conveyor assembly 245, at least partially due to the shear force exerted by the bifold clamps 235, the bifold clamps 235 may continue to pull the leading end portion 250 toward the folding drum 230 as the folding drum 230 rotates. Therefore, the surface of the first vacuum conveyor 270a may be configured to move at a relatively slow speed in the same direction as the leading end portion 250 is moving (i.e., toward the folding drum 230), and the relative speed between the leading end portion 250 and the surface of the first vacuum conveyor 270a during engagement may be reduced along with the undesirable effects typically associated with a higher relative speed engagement. In some embodiments, the first vacuum conveyor 270a may engage the leading end portion 250 when the leading end portion 250 is still held to the movable surface 232b peel conveyor assembly 245. In such an embodiment, it may be desirable to completely stop the movable surface of the first vacuum conveyor 270a prior to engaging the leading end portion 250.

Figure 5:
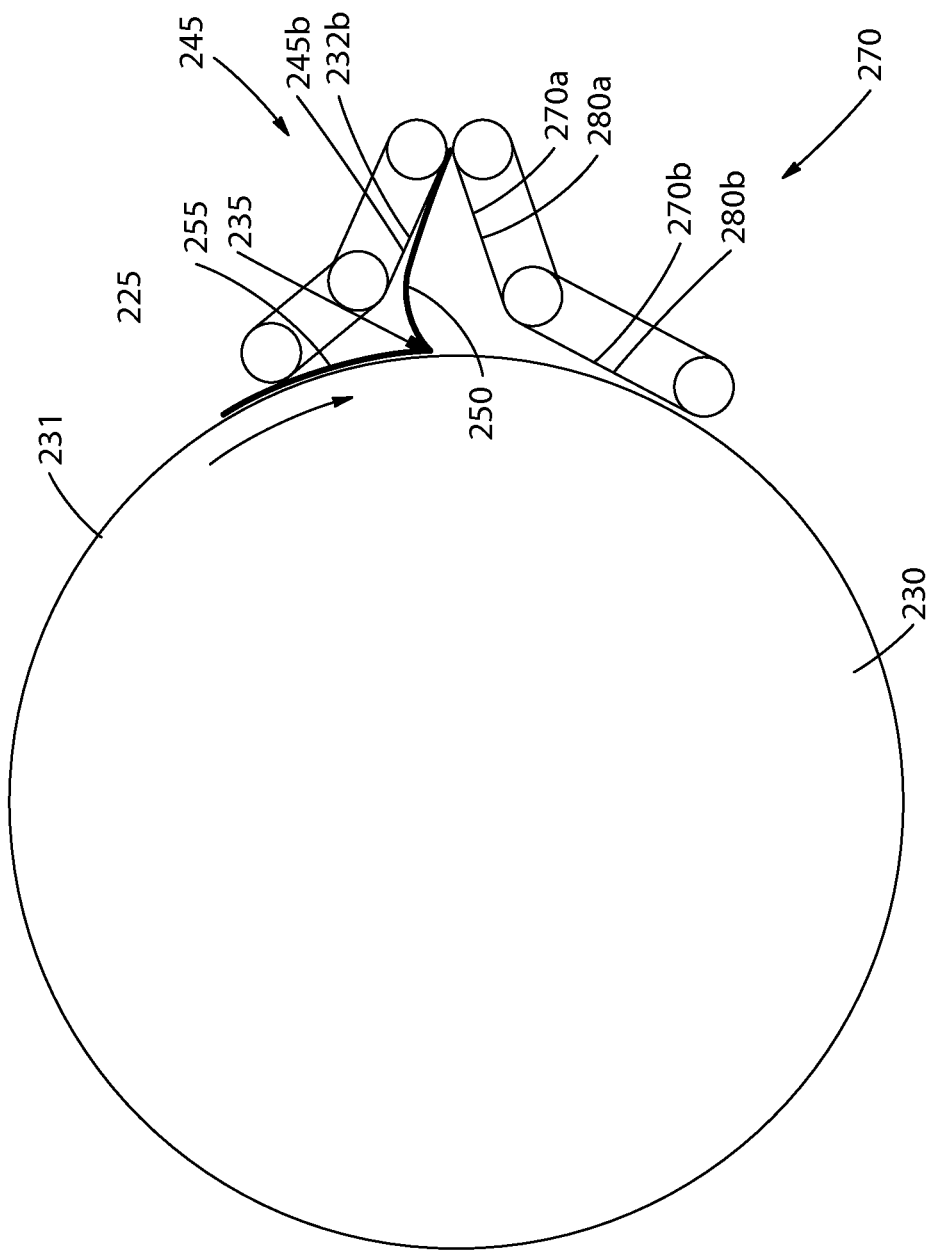
FIG. 5 is a detailed schematic view the article folding apparatus of FIG. 4 showing the leading end portion of the article being transferred to a second conveyor assembly.
Figure 6:
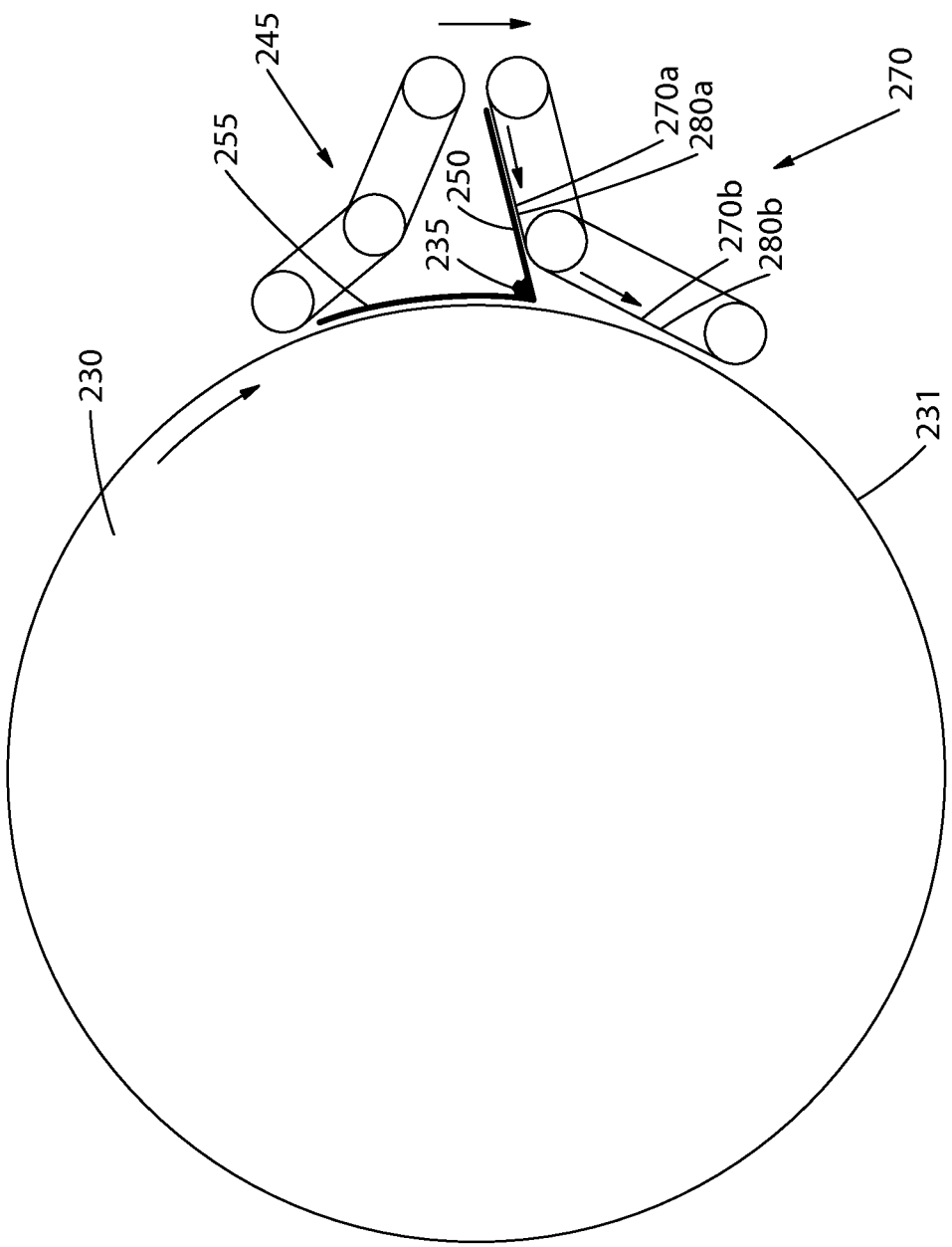
FIG. 6 is a detailed schematic view the article folding apparatus of FIG. 5 showing the leading end portion of the article transferred to a second conveyor assembly.

Upon engaging the leading end portion 250, the bifold conveyor assembly 270 may be configured to apply vacuum pressure to the leading end portion 250, such as shown for example in FIG. 5. It some embodiments, the suction exerted by the bifold conveyor assembly 270 may be strong enough to overcome the peel-force exerted by the peel conveyor assembly 245. In certain embodiments, it may be desirable to reduce or remove the peel-force exerted by the peel conveyor assembly 245 when the absorbent article 225 reaches a desired position or when the bifold conveyor assembly 280 engages the leading end portion 250. In some embodiments, the bifold conveyor assembly 280 may engage the leading end portion 250 when the leading end portion 250 begins to slip on the movable surface 232b of the second conveyor due to the force exerted on the leading end portion 250 by the clamps 235. In certain embodiments, the vacuum conveyor 280 may engage the leading end portion 250 when the leading end portion 250 is traveling in substantially the same direction as the movable surface 270a (e.g., after the leading end portion separates from the peel conveyor assembly 245). In certain embodiments, the movable surface 280a of the first vacuum conveyor 280a may be accelerated after engaging the leading end portion 250 to match the surface speed of the folding drum 230. In this way, the leading end portion 250 and the trailing end portion 255 may be traveling at substantially the same speed when the two portions 250, 255 are brought together in a face-to-face relationship. It should also be appreciated that the surface of the first vacuum conveyor 280a may accelerated during or even prior to engaging the leading portion 250.

In some instances, a portion of the movable surface 280a of the first vacuum conveyor 280a may be traveling in substantially the opposite direction as the movable surface 232b of the second conveyor 245b on the peel conveyor assembly 245. Consequently any premature engagement of the first vacuum conveyor 280a with the leading end portion 250 such as, for example, before the leading end portion 250 separates from the movable surface 232b of the second conveyor 245b may undesirably impact the bifold process. In order to reduce the possibility of premature engagement of the vacuum conveyor 280 with the leading end portion 250, a suitable distance or gap between the movable surface 232b of the peel conveyor assembly 245 and the movable surface 280a of the bifold conveyor assembly 270 when the bifold conveyor 280 is not engaged with as well as when engaging with the leading end portion 250. In some embodiments, the movable surfaces 280a, 280b of the bifold conveyor assembly 280 may be positioned relative to the peel conveyor assembly 245 and/or folding drum 230 by a positioning mechanism mechanically coupled to the bifold conveyor assembly. In some embodiments, the movable surfaces 232a, 232b of the bifold conveyor assembly 245 may also be positioned relative to the peel conveyor assembly 270 and/or folding drum 230 by a positioning mechanism mechanically coupled to the bifold conveyor assembly. Such positioning mechanisms may include for example, one or more cams, pistons, gears, pulleys, and the like.

The positioning mechanism may be configured to automatically vary the distance between the movable surface 280a of the first vacuum conveyor 280a and the movable surface 232b of the peel conveyor assembly 245 in a continuous or intermittent fashion. In certain embodiments, the distance between the surface of the folding drum 230 and the movable surfaces 232a, 232b of the vacuum conveyor 280 may be held constant or also varied. In some embodiments, the movement of the first vacuum conveyor 270a may pause at a particular position during the bifold process, for example, at the "top of the upstroke" (i.e., when the distance between the movable surface 280a of first vacuum conveyor 270a and the movable surface 232b of the second conveyor 245b is at a minimum), the "bottom of the downstroke" (i.e., when the distance between the movable surface 280a of first vacuum conveyor 270a and the movable surface 232b of the second conveyor 245b is at a maximum), and/or upon engaging the leading end portion 250. The positioning mechanism may have any suitable stroke length, for example, a stroke length of greater than 1 mm, between 1 mm and 20 cm, 1 mm and 20 mm, 1 mm and 10 mm, or even 1 mm and 5 mm. FIG. 5 shows an example of the first vacuum conveyor 270a at the "top of the upstroke," and FIG. 7 shows an example of the first vacuum conveyor 270a at the "bottom of the downstroke."

The positioning mechanism may be configured to suitably position the first vacuum conveyor 270a for engaging the leading end portion 250 during the "upstroke" (i.e., when the movable surface 280a of the first vacuum conveyor 270a is being moved closer to the movable surface 232b of the second conveyor 245b) and to provide a suitable gap between the vacuum conveyor 280 and the peel conveyor 245 during the "downstroke" (i.e., when the movable surface 280a of the first vacuum conveyor 270a is being moved away from the movable surface 232b of the second conveyor 245b). FIG. 4 shows an example of the first conveyor 270a during the "upstroke," and FIG. 6 shows an example of the first conveyor 270a during the "downstroke." In certain embodiments, the positioning mechanism may be configured such that the leading end portion 250 is transferred to the vacuum conveyor 280 at the top of the upstroke. Additionally or alternatively, the position of the movable surface 232b of ht second conveyor 245b may be moved relative to the movable surface 280a of the first conveyor 280a. Some gap distances may be at least greater than the thickness of the absorbent article 225, for example, greater than 1 mm, between 1 mm and 20 cm, or even between 1 mm and 20 mm. A method of providing a gap may include a bifold conveyor assembly 270 that includes a cam with a 3 mm stroke length for continuously varying the position of the first vacuum conveyor 280a surface relative to the movable surface 232b.

Figure 7:
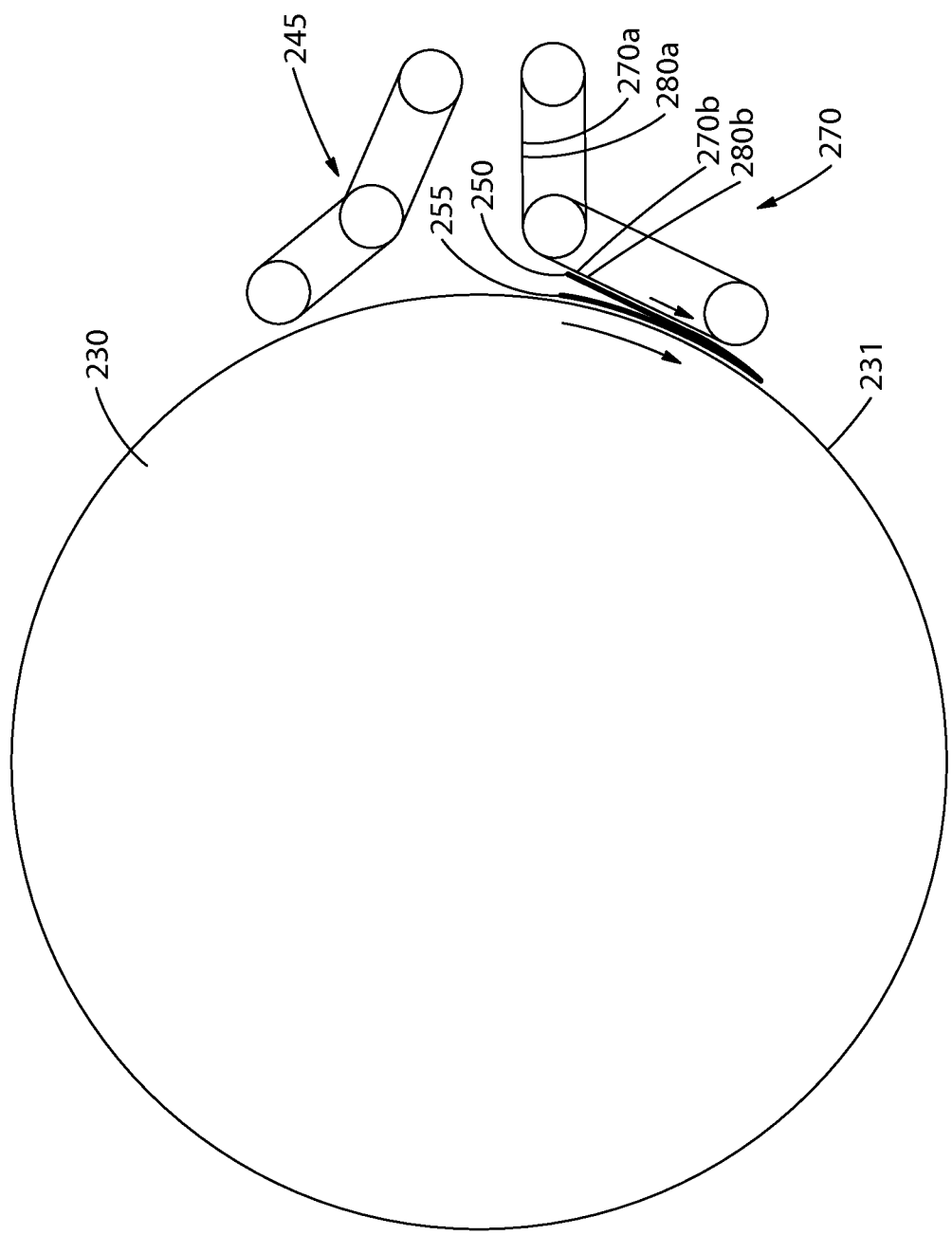
FIG. 7 is a detailed schematic view the article folding apparatus of FIG. 6 showing the article being folded between the folding drum and the second conveyor assembly.

As shown in FIG. 7, the leading end portion 250 is accelerated, carried toward, and transferred to the second vacuum conveyor 270b from the first conveyor 270a. At the time of transfer, the belt speed of the first conveyor 270a may substantially match the belt speed of the second conveyor 270b. After receiving the leading end portion 250, the second vacuum conveyor 270b transports the leading end portion 250 toward the folding drum 230 at a constant speed (e.g., the surface speed of the folding drum) until the leading end portion 250 and the trailing end portion 255 of the article 225 are aligned in a bifolded configuration.

At location E in FIG. 2, the leading end portion 290 of the folded article 225 may be subjected to further processes, such as optionally entering into glue compression rolls 295, where components of the absorbent article 225 may be adhesively joined to themselves or other components, as desired. The article may then be transported to a pair of compression rolls 298 to reinforce the optional adhesive bond(s) with high-pressure bonding. The processes at location E may be suitably configured for forming the bifolded article 225 into, e.g., a training pant product.

The method of operation of the folding apparatus 200 may described with reference to the figures herein and in the context of a method for folding articles, such as taped diapers or diaper pants. The articles advance in a machine direction and are to be folded along a cross directional fold line. Each article includes a leading end portion and a trailing end portion and having a first surface disposed opposite of a second surface. The articles are received onto a drum having an outer surface such that a first surface, such as a backsheet, of the article is engaged with the outer surface of the drum. The drum is rotated to move the outer surface at a first surface speed and transport the article in the machine direction. A second surface, such as a topsheet, of the leading end portion of the article engages a first conveyor comprising a movable surface traveling at the first speed. The leading end portion is transferred from the drum to the first conveyor. The second surface of the leading end portion of the article is then transferred from the first conveyor to a second conveyor comprising a movable surface traveling at the first speed. The movable surface of the second conveyor is decelerated to a second speed, which may be zero or stopped. A third conveyor comprising a movable surface traveling at the second speed is moved to engage the first surface of the leading end portion of the article. The leading end portion of the article is then transferred from the second conveyor to the third conveyor, and the movable surface of the third conveyor is accelerated from the second speed to the first speed. Next, the first surface of the leading end portion of the article is transferred from the third conveyor to a fourth conveyor comprising a movable surface traveling at the first speed. And the leading end portion of the article is transferred from the fourth conveyor onto the trailing end portion of the article on the drum.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for folding articles advancing in a machine direction along a cross directional fold line, each article having a leading end portion and a trailing end portion and having a first surface disposed opposite of a second surface, the apparatus comprising:

a drum having an outer surface, the drum adapted to rotate the outer surface at a first surface speed, wherein the outer surface of the drum is adapted to receive the first surface of each article and transport each article in the machine direction;

a first conveyor assembly comprising:
 a first vacuum conveyor comprising a movable surface adapted to travel at the first surface speed, wherein the movable surface of the first conveyor is adapted to receive the second surface of the leading end portion of each article from the drum;
 a second vacuum conveyor comprising a movable surface adapted to travel at the first surface speed and at a second surface speed, wherein the movable surface of the first vacuum conveyor is adapted to receive the second surface of the leading end portion of each article from the first conveyor; and a second conveyor assembly comprising:
 a third vacuum conveyor comprising a movable surface adapted to travel at the first surface speed and at the second surface speed, wherein the movable surface of the third vacuum conveyor is adapted to receive the first surface of the leading end portion of each article from the second conveyor;
 a fourth vacuum conveyor comprising a movable surface adapted to travel at the first speed, wherein the movable surface of the fourth vacuum conveyor is adapted to receive the first surface of the leading end portion of each article from the third conveyor.

2. The apparatus of claim 1, wherein the second speed is less than the first speed.

3. The apparatus of claim 2, wherein the second speed is zero.

4. The apparatus of claim 1, defining a minimum distance between the movable surface of the third vacuum conveyor and the movable surface of the second vacuum conveyor, and further comprising a positioning mechanism connected with the third vacuum conveyor, the positioning mechanism being configured move the third vacuum conveyor to change the minimum distance from a first distance to a second distance, wherein the first distance is less than the second distance.

5. The apparatus of claim 1, wherein the drum includes a clamp configured to selectively engage the second surface of each article held to the outer surface of the drum as the drum rotates.

6. The apparatus of claim 5, wherein the clamp engages each article along the fold line.

7. The apparatus of claim 1, wherein the drum comprises a vacuum to hold the first surface of each article against the outer surface of the drum.

8. A method for folding articles advancing in a machine direction along a cross directional fold line, each article having a leading end portion and a trailing end portion and having a first surface disposed opposite of a second surface, the method comprising the steps of:

receiving an article onto a drum having an outer surface such that the first surface of the article is engaged with the outer surface of the drum;
rotating the drum to move the outer surface at a first surface speed and transport the article in the machine direction;
engaging the second surface of the leading end portion of the article with a first conveyor comprising a movable surface traveling at the first speed;
transferring the leading end portion of the article from the drum to the first conveyor;
transferring the second surface of the leading end portion of the article from the first conveyor to a second conveyor comprising a movable surface traveling at the first speed;
decelerating the movable surface of the second conveyor to a second speed;
moving a third conveyor comprising a movable surface traveling at the second speed to engage the first surface of the leading end portion of the article;
transferring the leading end portion of the article from the second conveyor to the third conveyor;
accelerating the movable surface of the third conveyor from the second speed to the first speed;
transferring first surface of the leading end portion of the article from the third conveyor to a fourth conveyor comprising a movable surface traveling at the first speed; and
transferring the leading end portion of the article from the fourth conveyor onto the trailing end portion of the article on the drum.

9. The method of claim 8, wherein the second speed is zero.

10. The method of claim 8, further comprising the step of clamping the second surface of the article on the drum.

11. The method of claim 10, wherein the clamping step further comprising engaging the article along the fold line.

12. The method of claim 8, further comprising the step of applying a vacuum to the first surface of the article on the outer surface of the drum.

* * * * *